(12) United States Patent
Richard

(10) Patent No.: US 7,901,704 B2
(45) Date of Patent: Mar. 8, 2011

(54) EMBOLIZATION

(75) Inventor: Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 192 days.

(21) Appl. No.: 12/193,462

(22) Filed: Aug. 18, 2008

(65) Prior Publication Data

US 2009/0053281 A1  Feb. 26, 2009

Related U.S. Application Data

(60) Provisional application No. 60/957,014, filed on Aug. 21, 2007.

(51) Int. Cl.
*A61F 2/00* (2006.01)
(52) U.S. Cl. ........................................................ 424/423
(58) Field of Classification Search .................. None
See application file for complete search history.

(56) References Cited

U.S. PATENT DOCUMENTS

| | | | |
|---|---|---|---|
| 4,897,255 A | 1/1990 | Fritzberg et al. | |
| 5,733,925 A | 3/1998 | Kunz et al. | |
| 6,368,658 B1 | 4/2002 | Schwarz et al. | |
| 7,053,134 B2 | 5/2006 | Baldwin et al. | |
| 2004/0076582 A1 | 4/2004 | Dimatteo et al. | |
| 2004/0101564 A1 | 5/2004 | Rioux et al. | |
| 2004/0186377 A1 | 9/2004 | Zhong et al. | |
| 2006/0116711 A1 | 6/2006 | Elliott et al. | |
| 2007/0083219 A1 | 4/2007 | Buiser et al. | |
| 2007/0083226 A1 | 4/2007 | Buiser et al. | |
| 2007/0141099 A1 | 6/2007 | Buiser et al. | |
| 2007/0141340 A1 | 6/2007 | Song | |
| 2007/0142859 A1 | 6/2007 | Buiser et al. | |
| 2007/0142893 A1 | 6/2007 | Buiser et al. | |
| 2008/0268058 A1* | 10/2008 | Keenan et al. | 424/489 |

OTHER PUBLICATIONS

Deible et al., "Molecular barriers to biomaterial thrombosis by modification of surface proteins with polyethylene glycol," Biomaterials, vol. 19, pp. 1885-1893, (1998).
Kolb et al., "The growing impact of click chemistry on druck discovery," Drug Discovery Today, vol. 8, No. 24, pp. 1128-1137, Dec. 24, 2003.
Michel et al., "A Comparison of 4 Radionuclides Conjugated to Antibodies for Single-Cell Kill," The Journal of Nuclear Medicine, vol. 44, No. 4, Apr. 2003.
Rostovtsev et al., "A Stepwise Huisgen Cycloaddition Process: Copper(I)-Catalyzed Regioselective "Ligation" of Azides and Terminal Alkynes," Angew. Chem. International Edition, vol. 41, No. 14, (2002).
Speers et al., "Activity-Based Protein Profiling in Vivo Using a Copper(I)-Catalyzed Azide-Alkyne [3+2] Cycloaddition," Journal of American Chemical Society, vol. 125, pp. 4686-4687, (2003).
Wang et al., "Bioconjugation by Copper(I)-Catalzed Azide-Alkyne [3+2] Cycloaddition," Journal of American Chemical Society, vol. 125, pp. 3192-3193, (2003).

* cited by examiner

*Primary Examiner* — Robert A Wax
*Assistant Examiner* — Bethany Barham
(74) *Attorney, Agent, or Firm* — Fish & Richardson P.C.

(57) ABSTRACT

Articles and methods that include a particle having a maximum dimension of at most 5,000 microns, and an embolic coil capable of binding to the particle, are disclosed.

13 Claims, 5 Drawing Sheets

EMBOLIZATION

CROSS-REFERENCE TO RELATED APPLICATION

This application is a utility from provisional of and claims priority under 35 U.S.C. §120 to U.S. Application Ser. No. 60/957,014, filed Aug. 21, 2007, the entire contents of which being hereby fully incorporated by reference.

TECHNICAL FIELD

This invention relates to embolization within body lumens, as well as related devices, systems and methods.

BACKGROUND

Therapeutic occlusions such as embolizations can be used to prevent or treat pathological conditions in body lumens. Embolic coils and embolic particles can be used to occlude vessels.

SUMMARY

In one aspect, the invention generally relates to an article that includes a particle having a maximum dimension of at most 5,000 microns, and an embolic coil bound to the particle.

In one aspect, the invention generally relates to an article that includes a particle having a maximum dimension of at most 5,000 microns, and an embolic coil capable of binding to the particle.

In another aspect, the invention generally relates to an article that includes a particle including a coating, and an embolic coil including a coating, where the particle has a maximum dimension of at most 5,000 microns, and the coating of the particle is bound to the coating of the embolic coil.

In a further aspect, the invention generally relates to an article that includes a particle including a ligand and an embolic coil including a ligand, where the particle has a maximum dimension of at most 5,000 microns, and the ligand of the particle is bound to the ligand of the embolic coil.

In another aspect, the invention generally relates to a method that includes bonding a particle to an embolic coil (e.g., in vivo) to release an agent from the embolic coil, the particle, or both, where the particle has a maximum dimension of at most 5,000 microns.

Embodiments can include one or more of the following features.

The particle can include a coating that capable of binding to the embolic coil.

The embolic coil can include a coating that is capable of binding to the particle. The article can further include a plurality of particles capable of binding to the embolic coil, each of the particles having a maximum dimension of at most 5,000 microns (e.g., at least 100 microns).

The particle can have a maximum dimension of at least 100 microns.

The article can further include a plurality of particles capable of binding to the embolic coil, each of the particles having a maximum dimension of at most 5,000 microns (e.g., at least 500 microns).

The embolic coil can include fibers.

The coating of the particle can be ionic. The coating of the embolic coil can be ionic. The coating of the particle can have a charge that is opposite to a charge of the coating of the embolic coil.

The coating of the particle can be ionically bound to the coating of the embolic coil. Alternatively, or in addition, the coating of the particle can be covalently bound to the coating of the embolic coil.

The coating of the particle can include a first material, the coating of the embolic coil can include a second material, and the first and second materials can be capable of undergoing an acid-base reaction, the first and second materials can be capable of undergoing a Michael addition, the first and second materials can be capable of undergoing an isocyanate-alcohol reaction, or the first and second materials can be capable of undergoing an azide-alkyne reaction.

The ligand of the embolic coil and the ligand of the particle can be ionically bound. The ligand of the embolic coil and the ligand of the particle can be covalently bound.

The ligand of the particle can include a first material, the ligand of the embolic coil can include a second material, and the first and second materials can be capable of undergoing an acid-base reaction, the first and second materials can be capable of undergoing a Michael addition, the first and second materials can be capable of undergoing an isocyanate-alcohol reaction, the first and second materials can be capable of undergoing an azide-alkyne reaction, or the first and second materials can be capable of forming a biotin-avidin complex.

The agent can include a therapeutic agent.

The method can include releasing the agent as the embolic coil and the particle are bound to each other.

The agent can be released from the particle in an ion-exchange reaction. A maximum dimension of the particle can increase following release of the agent.

Embodiments can include one or more of the following advantages.

Embolic coils and particles can interact and bind with one another (e.g., by forming bonds such as ionic and/or covalent bonds) and the particles can remain bound to the coils at an embolization site. This can result in a more efficient embolization procedure.

One or more therapeutic agents can be released during the binding between embolic particles and coils. The therapeutic agents can be used to perform a wide variety of functions, including providing anti-tumor function, clotting and anti-clotting functions, and pain management functions. Because of the localization of embolic particles due to binding with embolic coils, the therapeutic agents can be delivered to lumen sites with high selectivity.

Ion-exchange reactions can be used to increase the maximum dimension of embolic particles as binding occurs between the particles and embolic coils. The can allow for flexibility in manipulating the size of the particles and/or coils in situ. As a result, the embolization procedure can be more efficient because occlusion of a vessel by the larger particles is more complete.

Other features and advantages of the invention will be apparent from the description, drawings, and claims.

DESCRIPTION OF DRAWINGS

Like reference symbols in the various drawings indicate like elements.

DETAILED DESCRIPTION

Figure 1:
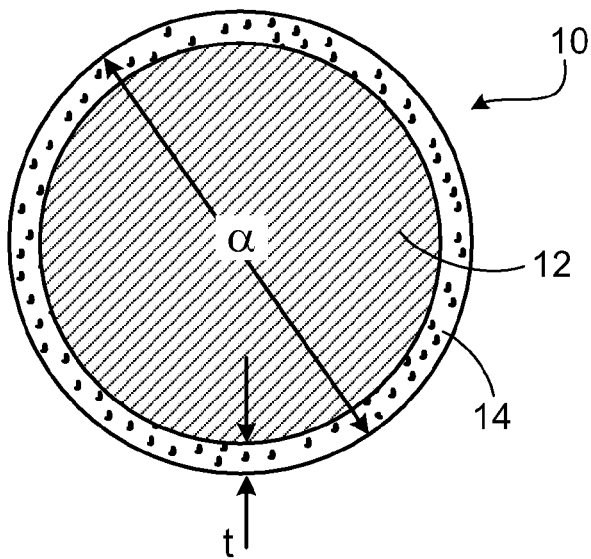
FIG. 1 is cross-sectional view of an embolic particle.

Embolic particles and coils can be used together to occlude body lumens. In particular, particles and coils that interact and subsequently bind to one another can be used to achieve efficient embolization of lumens. FIG. 1 is a cross-sectional view of an embolic particle 10. Embolic particle 10 includes a core 12, a coating 14 of average thickness t measured along a radial line extending from a center of mass of particle 10, and a maximum dimension d measured along a line extending through the center of mass of particle 10.

Figure 2:
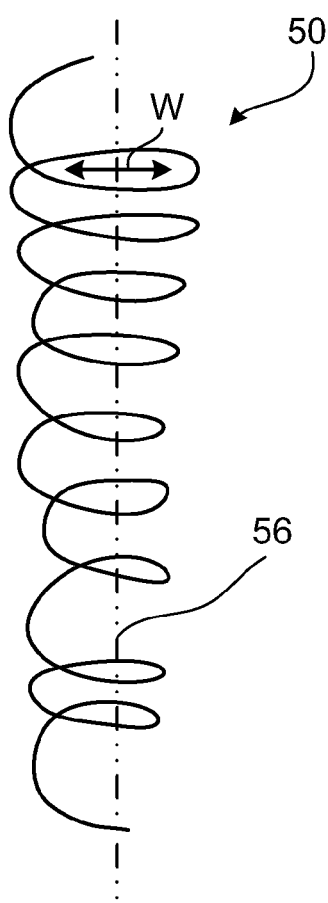
FIG. 2 is a schematic view of an embolic coil.
Figure 3:
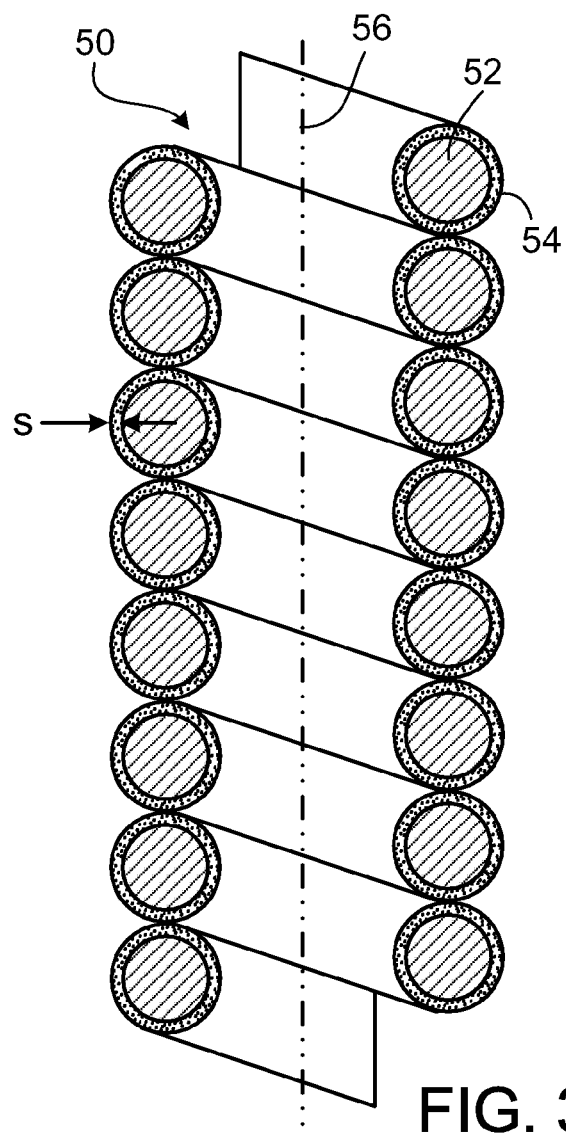
FIG. 3 is a cross-sectional view of an embolic coil.

FIGS. 2 and 3 show schematic and cross-sectional views, respectively, of an embolic coil 50. Embolic coil 50 includes a core 52 and a coating 54 on core 52. Coil 50 has a diameter w measured in a direction orthogonal to longitudinal axis 56.

In general, core 52 of embolic coil 50 is formed of windings of wire. For example, in some embodiments, core 52 is formed from windings of wire that include one or more metals or metal alloys, such as platinum, platinum alloys (e.g., a platinum-tungsten alloy), stainless steel, Nitinol, and Elgiloy®.

Figure 4:
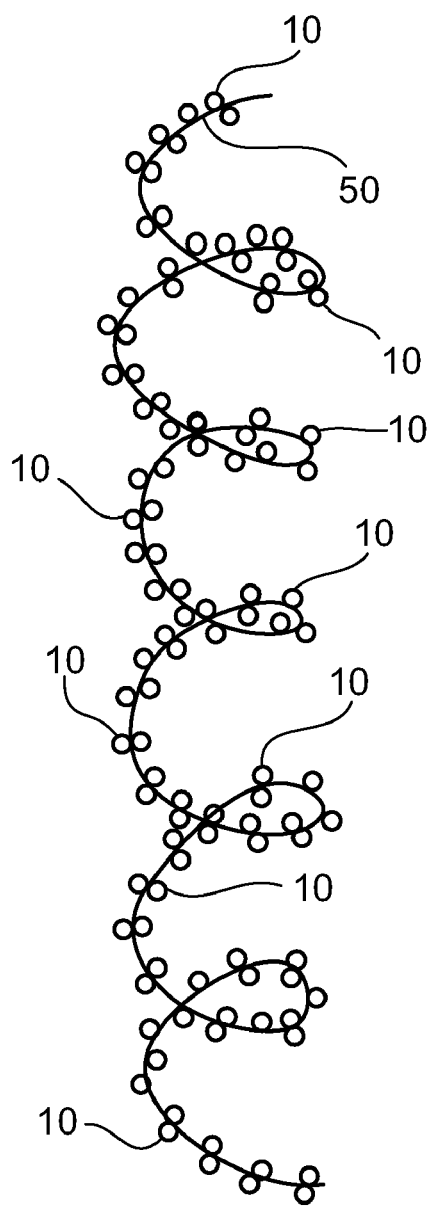
FIG. 4 is a schematic view of a plurality of embolic particles bound to an embolic coil.

The compositions of coatings 14 and 54 are generally chosen such that coatings 14 and 54 include at least one pair of complementary agents that cause embolic particle 10 to bind to a surface of embolic coil 50 (e.g., in vivo). For example, the complementary agents can be one or more ligands that react chemically or otherwise interact to bind particle 10 to a surface of coil 50. FIG. 4 shows a plurality of embolic particles 10 bound to a surface of embolic coil 50. Typically, one or more embolic coils 50 are first delivered to a selected body lumen in order to initiate formation of an occlusion. Thereafter, embolic particles are delivered to the same lumen. An interaction occurs between one or more agents in each of coatings 14 and 54, causing embolic particles 10 to adhere to surfaces of embolic coils 50. The attachment of embolic particles 10 to embolic coils 50 can help to further occlude the selected body lumen.

In some embodiments, coatings 14 and 54 include oppositely charged ionic constituents so that an ionic bond is formed between embolic particles 10 and embolic coils 50. For example, either coating 14 or coating 54 can include positively-charged chemical species such as quaternary nitrogen-containing groups. The other coating can include negatively-charged chemical species such as sulfonate-containing groups, for example. When the oppositely charged embolic particles 10 and embolic coils 50 are introduced into a selected body lumen, ionic bonds form between coatings 14 and 54 of the particles and coils, respectively. As a result, the particles remain bound to coil surfaces and are not carried by fluids in the lumen to other body sites.

In some embodiments, coatings 14 and 54 include one or more agents (e.g., ligands) that react chemically with one another, forming bonds between coatings 14 and 54. For example, in certain embodiments, either coating 14 or coating 54 can include an acidic agent, and the other coating can include a basic agent, such that an acid-base reaction can occur between the agents in coatings 14 and 54, forming ionic bonds between the two coatings. Exemplary coating materials with suitable acidic agents include materials such as carboxylic acids, sulfonic acids, and phosphonic acids. Exemplary coating materials with suitable basic agents include materials such as primary, secondary, and tertiary amines.

In some embodiments, coatings 14 and 54 include complementary agents (e.g., ligands) that undergo a Michael addition reaction. For example, either coating 14 or coating 54 can include one or more Michael acceptors. Typically, Michael acceptors include activated double bonds where an electron-withdrawing group is bonded directly to one of the carbon atoms of the double bond. Examples of electron-withdrawing groups include C=O, C(O)O, S=O, or $SO_2$. In certain embodiments, coatings 14 or 54 can include moieties that function as Michael acceptors such as α,β-unsaturated ketones, α,β-unsaturated esters, other α,β-unsaturated carbonyl moieties, acrylate moieties, acrylamide moieties, and vinylsulfone moieties. In some embodiments, coatings 14 or 54 can include cyclic moieties that function as Michael acceptors such as, for example, maleimide, quinone, and/or vinylpyridinium groups. In certain embodiments, for example, Michael acceptor moieties are attached to multi-arm polymer chains. For example, coating 14 or 54 can be formed from multi-arm polyethylene glycol acrylates.

The other coating can include one or more Michael donors. Typically, Michael donors include nucleophilic moieties such as thiols, amines, cyano groups, acyl groups, nitro groups, hydroxyl groups, malonates, cyanoacetates, acetoacetates, and/or other β-keto esters. Exemplary coating materials that function as Michael donors include cysteine-containing proteins and/or polypeptides, and thiolated polysaccharides.

When coatings 14 and 54 are in proximity (e.g., when particles 10 and coils 50 are introduced into the same body lumen), a Michael addition reaction can occur between donors and acceptors. As a result of the Michael addition reaction, covalent bonds are formed between coatings 14 and 54, and particles 10 are bound to surfaces of coils 50.

In some embodiments, coatings 14 and 54 include complementary agents (e.g., ligands) that undergo an isocyanate-alcohol reaction. For example, either coating 14 or coating 54 can include one or more isocyanates, and the other coating can include one or more alcohols. When coatings 14 and 54 are in proximity, an isocyanate-alcohol reaction can occur between the complementary agents in coatings 14 and 54. As a result of the reaction, covalent bonds are formed between coatings 14 and 54, and particles 10 are bound to surfaces of coils 50. Exemplary conditions for such reactions are disclosed, for example, in Deible, C. R. et al., *Biomaterials* 1998, 19, 1885-1893. Exemplary coating materials that include isocyanates are isocyanate-terminated polyethylene glycols and poly(isocyanatoethylmethacrylate). Exemplary coating materials that include alcohols are poly-HEMA, poly-HEA, and polyvinyl alcohol.

More generally, coatings 14 and 54 can include isocyanates and/or isothiocyanates that react with complementary agents. For example, isocyanates in coatings 14 and/or 54 can react with amines and thiols, in addition to alcohols. Exemplary coating materials that include amines and thiols are polyethyleneimines, chitosan, and cysteine-containing proteins. Isothiocyanates in coatings 14 and/or 54 can react with alcohols, amines, and thiols. Standard conditions can be used to promote such reactions.

In some embodiments, coatings 14 and 54 include complementary agents (e.g., ligands) that undergo an azide-alkyne reaction. For example, either coating 14 or coating 54 can include one or more azides, and the other coating can include one or more alkynes. Coating materials that can have pendant azide and/or alkyne groups include, for example, polyvinyl alcohols, polyHEMAs, carbohydrates, polyethylene oxides, polyethylene glycols, polyhydroxyethyl acrylates, polyacrylamides, polymethacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, and poly(lactic-co-glycolic) acids (e.g., poly(d-lactic-co-glycolic) acids).

The azide and alkyne moieties can be reacted, for example, via a cycloaddition reaction, such as the Huisgen azide-alkyne [3+2] cycloaddition reaction. Exemplary conditions for such reactions are disclosed, for example, in Kolb, H. C. et al., *Drug Discovery Today* 2003, 8, 1128-1137; Speers, A. E. et al., *J. Am. Chem. Soc.* 2003, 125, 4686-4687; Yang Q. et al., *J. Am. Chem. Soc.* 2003, 125, 3192-3193; Rostovtsev V. V. et al., *J. Am. Chem. Soc.* 2002, 41, 2596-2599; Rostovtsev V. V. et al., *Angew. Chem., Int. Ed.* 2002, 41, 2596-2599. As a result of the azide-alkyne reaction, covalent bonds are formed between coatings 14 and 54, and particles 10 are bound to surfaces of coils 50.

In some embodiments, coatings 14 and 54 include one or more magnetic materials that produce magnetic attractive forces between coatings 14 and 54, binding particles 10 and coils 50 together in body lumens. For example, coatings 14 and 54 can each include one or more ferromagnetic materials. As used herein, a ferromagnetic material refers to a material that has a magnetic susceptibility of at least 0.075 or more (e.g., at least 0.1 or more, at least 0.2 or more, at least 0.3 or more, at least 0.4 or more, at least 0.5 or more, at least one or more, at least ten or more, at least 100 or more, at least 1,000 or more, at least 10,000 or more) when measured at 25° C. Suitable ferromagnetic materials include, for example, a metal (e.g., a transition metal such as nickel, cobalt, or iron), a metal alloy (e.g., a nickel-iron alloy such as Mu-metal), a metal oxide (e.g., an iron oxide such as magnetite), a ceramic nanomaterial, a soft ferrite (e.g., nickel-zinc-iron), a magnet alloy (e.g., a rare earth magnet alloy such as a neodymium-iron-boron alloy or a samarium-cobalt alloy), an amorphous alloy (e.g., iron-silicon-boron), a non-earth alloy, or a silicon alloy (e.g., an iron-zirconium-copper-boron-silicon alloy, an iron-zirconium-copper-boron-silicon alloy). Magnetite is commercially available from FerroTec Corporation (Nashua, N.H.), under the tradename EMG 1111 Ferrofluid. Iron-copper-niobium-boron-silicon alloys are commercially available from Hitachi Metals of America under the tradename Finemet™. Iron-zirconium-copper-boron-silicon alloys are commercially available from MAGNETEC GmbH under the tradename Nanoperm®. When coating 14 includes one or more magnetic materials, an external magnetic source (e.g., a magnetic wand) can be used to direct embolic particles 10 to a specific site within a body lumen.

In some embodiments, bonds can be formed between coatings 14 and 54 via the formation of biotin-avidin complexes between constituents of coatings 14 and 54. For example, one of coatings 14 and 54 can include one or more biotin species, and the other coating can include avidin species. When particles 10 and coils 50 are in proximity, a complexation event can occur where biotin species are complexed by avidin species, forming bonds between coatings 14 and 54. As a result, particles 10 are bound to coils 50 at a selected lumen site.

A wide variety of different therapeutic agents can be present in coatings 14 and/or 54, and can be released as a result of interactions between the coatings that lead to binding of embolic particles and coils. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; proteins; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Examples of radioactive species include yttrium ($^{90}$Y), holmium ($^{166}$Ho), phosphorus ($^{32}$P), ($^{177}$Lu), actinium ($^{225}$Ac), praseodymium, astatine ($^{211}$At), rhenium ($^{16}$Re), bismuth ($^{212}$Bi or $^{213}$Bi),), samarium ($^{153}$Sm), iridium ($^{192}$Ir), rhodium ($^{105}$Rh), iodine ($^{131}$I or $^{125}$I), indium ($^{111}$In), technetium ($^{99}$Tc), phosphorus ($^{32}$P), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe)selenium ($^{75}$Se), and/or gallium ($^{67}$Ga). In some embodiments, yttrium ($^{90}$Y), lutetium ($^{177}$Lu), actinium ($^{225}$Ac), praseodymium, astatine ($^{211}$At), rhenium ($^{16}$Re), bismuth ($^{212}$Bi or $^{213}$Bi), holmium ($^{166}$Ho), samarium ($^{153}$Sm), iridium ($^{192}$Ir), and/or rhodium ($^{105}$Rh) can be used as therapeutic agents. In certain embodiments, yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), holmium ($^{166}$Ho), samarium ($^{153}$Sm), iridium ($^{192}$Ir), rhodium ($^{105}$Rh), iodine ($^{131}$I or $^{125}$I), indium ($^{111}$In), technetium ($^{99}$Tc), phosphorus ($^{32}$P), carbon ($^{14}$C), and/or tritium ($^{3}$H) can be used as a radioactive label (e.g., for use in diagnostics). In some embodiments, a radioactive species can be a radioactive molecule that includes antibodies containing one or more radioisotopes, for example, a radiolabeled antibody. Radioisotopes that can be bound to antibodies include, for example, iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$Tc), phosphorus ($^{32}$P), rhodium ($^{105}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), and/or gallium ($^{67}$Ga). Examples of antibodies include monoclonal and polyclonal antibodies including RS7, Mov18, MN-14 IgG, CC49, COL-1, mAB A33, NP-4 F(ab')2 anti-CEA, anti-PSMA, ChL6, m-170, or antibodies to CD20, CD74 or CD52 antigens. Examples of radioisotope/antibody pairs include m-170 MAB with $^{90}$Y. Examples of commercially available radioisotope/antibody pairs include Zevalin™ (IDEC pharmaceuticals, San Diego, Calif.) and Bexxar™ (Corixa corporation, Seattle, Wash.). Further examples of radioisotope/antibody pairs can be found in *J. Nucl. Med. April,* 2003: 44(4): 632-40.

Non-limiting examples of therapeutic agents include anti-thrombogenic agents; thrombogenic agents; agents that promote clotting; agents that inhibit clotting; antioxidants; angiogenic and anti-angiogenic agents and factors; anti-proliferative agents (e.g., agents capable of blocking smooth muscle cell proliferation, such as rapamycin); calcium entry blockers (e.g., verapamil, diltiazem, nifedipine); targeting factors (e.g., polysaccharides, carbohydrates); agents that can stick to the vasculature (e.g., charged moieties, such as gelatin, chitosan, and collagen); and survival genes which protect against cell death (e.g., anti-apoptotic Bcl-2 family factors and Akt kinase).

Examples of non-genetic therapeutic agents include: antithrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Examples of genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them.

Vectors of interest for delivery of genetic therapeutic agents include: plasmids; viral vectors such as adenovirus (AV), adenoassociated virus (AAV) and lentivirus; and non-viral vectors such as lipids, liposomes, and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents are disclosed in Kunz et al., U.S. Pat. No. 5,733,925, which is incorporated herein by reference. Therapeutic agents disclosed in this patent include the following: "Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

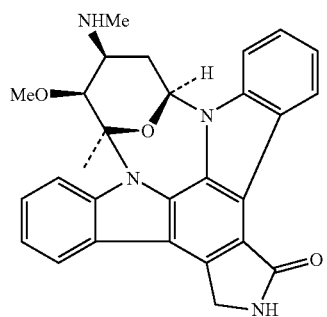

as well as diindoloalkaloids having one of the following general structures:

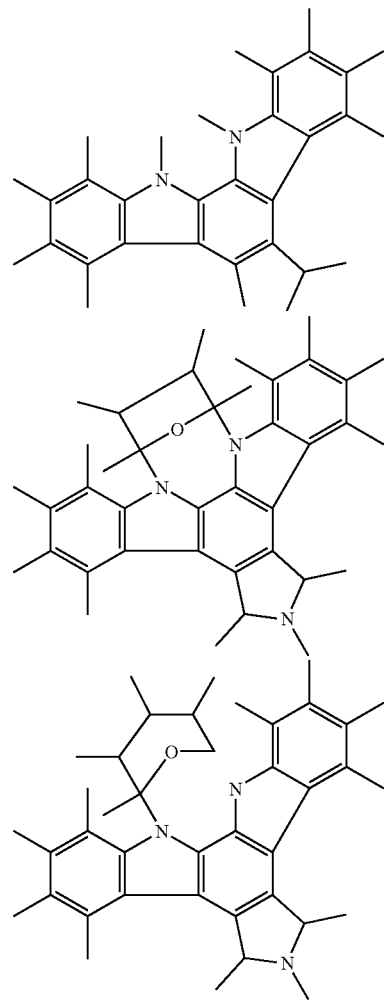

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, *Pseudomonas* exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, *Pseudomonas* exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP Iib/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), Fxa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclins and prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, anti-sense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, interleukins, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

In some embodiments, a therapeutic agent can be hydrophilic. An example of a hydrophilic therapeutic agent is doxorubicin hydrochloride. In certain embodiments, a therapeutic agent can be hydrophobic. Examples of hydrophobic therapeutic agents include paclitaxel, cisplatin, tamoxifen, and doxorubicin base. In some embodiments, a therapeutic agent can be lipophilic. Examples of lipophilic therapeutic agents include taxane derivatives (e.g., paclitaxel) and steroidal materials (e.g., dexamethasone).

Therapeutic agents are described, for example, in DiMatteo et al., U.S. Patent Application Publication No. US 2004/0076582 A1, published on Apr. 22, 2004, and entitled "Agent Delivery Particle"; Schwarz et al., U.S. Pat. No. 6,368,658; Buiser et al., U.S. patent application Ser. No. 11/311,617, filed on Dec. 19, 2005, and entitled "Coils"; and Song, U.S. patent application Ser. No. 11/355,301, filed on Feb. 15, 2006, and entitled "Block Copolymer Particles", all of which are incorporated herein by reference.

Coatings 14 and/or 54 can also include other materials. For example, coatings 14 and/or 54 can include one or more radiopaque materials to increase the visibility of embolic particles and/or coils in x-ray fluorescence imaging measurements. A radiopaque material can be, for example, a metal (e.g., tungsten, tantalum, platinum, palladium, lead, gold, titanium, silver), a metal alloy (e.g., stainless steel, an alloy of tungsten, an alloy of tantalum, an alloy of platinum, an alloy of palladium, an alloy of lead, an alloy of gold, an alloy of titanium, an alloy of silver), a metal oxide (e.g., titanium dioxide, zirconium oxide, aluminum oxide), bismuth subcarbonate, or barium sulfate. In some embodiments, a radiopaque material is a radiopaque contrast agent. Examples of radiopaque contrast agents include Omnipaque™, Renocal®, iodiamide meglumine, diatrizoate meglumine, ipodate calcium, ipodate sodium, iodamide sodium, iothalamate sodium, iopamidol, and metrizamide. Radiopaque contrast agents are commercially available from, for example, Bracco Diagnostic.

In some embodiments, coatings 14 and/or 54 can include one or more MRI-visible materials for enhancing visibility of embolic particles and/or coils in MRI measurements. An MRI-visible material can be, for example, a non-ferrous metal-alloy containing paramagnetic elements (e.g., dysprosium or gadolinium) such as terbium-dysprosium, dysprosium, and gadolinium; a non-ferrous metallic band coated with an oxide or a carbide layer of dysprosium or gadolinium (e.g., $Dy_2O_3$ or $Gd_2O_3$); a non-ferrous metal (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; or nanocrystalline particles of the transition metal oxides (e.g., oxides of Fe, Co, Ni). In certain embodiments, an MRI-visible material can be an MRI contrast agent. Examples of MRI contrast agents include superparamagnetic iron oxides (e.g., ferumoxides, ferucarbotran, ferumoxsil, ferumoxtran (e.g., ferumoxtran-10), PEG-feron, ferucarbotran); gadopentetate dimeglumine; gadoterate meglumine; gadodiamide; gadoteridol; gadoversetamide; gadobutrol; gadobenate dimeglumine; mangafodipir trisodium; gadoxetic acid; gadobenate dimeglumine; macromolecular Gd-DOTA derivate; gadobenate dimeglumine; gadopentetate dimeglumine; ferric ammonium citrate; manganese chloride; manganese-loaded zeolite; ferristene; perfluoro-octylbromide; and barium sulfate. MRI contrast agents are described, for example, in U.S. patent application Ser. No. 10/390,202, now U.S. Publication No. US 2004/0186377, filed on Mar. 17, 2003 and entitled "Medical Device", the entire contents of which are incorporated herein by reference.

Radiopaque materials, MRI-visible materials, ferromagnetic materials, and contrast agents, any or all of which can be included in coatings 14 and/or 54, are described, for example, in Rioux et al., U.S. Patent Application Publication No. US 2004/0101564 A1, published on May 27, 2004, and entitled "Embolization", the entire contents of which are incorporated herein by reference.

In some embodiments, the maximum dimension d of embolic particle 10 is at most 5,000 microns. For example, in certain embodiments, d is 4,500 microns or less (e.g., 4,000 microns or less, 3,500 microns or less, 3,000 microns or less, 2,000 microns or less). In some embodiments, d is ten microns or more (e.g., 50 microns or more, 100 microns or more, 200 microns or more, 300 microns or more, 500 microns or more, 700 microns or more, 1,000 microns or more, 1,200 microns or more). In certain embodiments, d can be in a range from 100 microns to 700 microns; from 500 microns to 700 microns; from 100 microns to 500 microns; from 100 microns to 300 microns; from 300 microns to 500 microns; from 500 microns to 1,200 microns; from 500 microns to 700 microns; from 700 microns to 900 microns; from 900 microns to 1,200 microns.

In general, core 12 can be formed of a variety of materials. For example, in some embodiments, core 12 is formed of one or more polymers. Examples of polymers include polyvinyl alcohols, polyacrylic acids, polymethacrylic acids, polyvinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids (e.g., poly (d-lactic-co-glycolic) acids), and copolymers or mixtures thereof. In certain embodiments, core 12 can be substantially formed of a highly water insoluble, high molecular weight polymer. An example of such a polymer is a high molecular weight polyvinyl alcohol (PVA) that has been acetalized. Core 12 can be substantially pure intrachain 1,3-acetalized PVA and substantially free of animal derived residue such as collagen. In some embodiments, the majority (e.g., at least 75 weight percent, at least 90 weight percent, at least 95 weight percent) of core 12 is formed of a bioabsorbable polymer (e.g., polysaccharide, such as alginate).

The shape of core 12 can generally be varied as desired. Typically, core 12 has a shape that is approximately spherical. However, in certain embodiments, the shape of core 12 can be non-spherical. For example, during fabrication, core 12 can be physically shaped (e.g., molded, compressed, and/or punched) so that core 12 adopts a non-spherical shape. Non-spherical cores can also be produced from spherical cores by post-fabrication steps including cutting the spherical cores. Methods for particle shaping are described, for example, in U.S. patent application Ser. No. 10/402,068, now U.S. Pat. No. 7,053,134, filed Mar. 28, 2003 and entitled "Forming a Chemically Cross-Linked Particle of a Desired Shape and Diameter", the entire contents of which are incorporated herein by reference.

The thickness t of coating 14 can be chosen as desired. For example, the thickness t can be chosen to control a total amount of the one or more agents in embolic particle 10. In some embodiments, t can be 10 nm or more (e.g., 20 nm or more, 50 nm or more, 100 nm or more, 200 nm or more, 300 nm or more, 400 nm or more, 500 nm or more). In certain embodiments, t can be 50 microns or less (e.g., 40 microns or less, 30 microns or less, 20 microns or less, 10 microns or less, 5 microns or less, 1 micron or less).

The thickness s of coating 54 is measured in a radial direction perpendicular to a longitudinal axis of core 52 (e.g., perpendicular to an axis extending in a direction orthogonal to the plane of FIG. 3). In general, s can be chosen to control a total amount of the one or more agents in embolic coil 50. In some embodiments, s can be 10 nm or more (e.g., 20 nm or more, 50 nm or more, 100 nm or more, 200 nm or more, 300 nm or more, 400 nm or more, 500 nm or more). In certain embodiments, s can be 50 microns or less (e.g., 40 microns or less, 30 microns or less, 20 microns or less, 10 microns or less, 5 microns or less, 1 micron or less).

Figure 5:
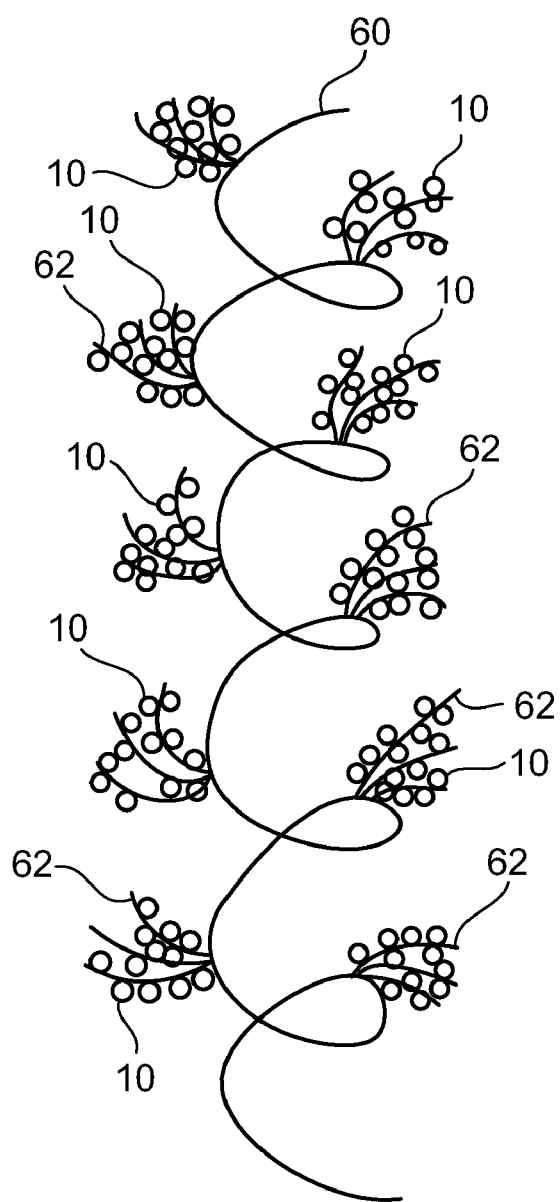
FIG. 5 is a schematic view of a plurality of embolic particles bound to an embolic coil that includes fibers.

In some embodiments, embolic coils can include fibers. FIG. 5 shows a schematic view of an embolic coil 60 that includes a plurality of fibers 62. Fibers 62 are attached to, and extend outward from, a surface of coil 60. In certain embodiments, fibers 62 can have a length of 0.5 mm or more (e.g., 1 mm or more, 1.5 mm or more, 2 mm or more, 2.5 mm or more). In some embodiments, fibers 62 can have a length of 5 mm or less (e.g., 4.5 mm or less, 4 mm or less, 3.5 mm or less, 3 mm or less).

Fibers 62 are typically formed from one or more flexible materials. For example, in some embodiments, fibers 62 can be formed from materials such as polyethylene terephthalate (e.g., Dacron®), nylon, and/or collagen.

In some embodiments, fibers 62 extend outward (e.g., radially outward) from the surface of embolic coil 60. As shown in FIG. 5, coating 54 can be deposited on the surface of fibers 62 so that particles 10 are bound to fibers 62 via interactions between coatings 14 and 54. Embolic particles 10 do not bind to the surface of embolic coil 60, which does not include a coating having agents that interact with complementary agents in coating 14. In certain embodiments, both embolic coil 60 and fibers 62 can include coating 54, so that embolic particles 10 bind both to surfaces of coil 60 and to surfaces of fibers 62.

In some embodiments, interactions between coatings 14 and 54 can lead to release of one or more agents from either or both of coatings 14 and 54. For example, one or more chemical reactions can occur between constituents of coatings 14 and 54, as discussed above, releasing one or more agents as a result. Alternatively, or in addition, one or more agents can be released from either or both of coatings 14 and 54 as a result of an ion-exchange process.

In certain embodiments, swelling of embolic particles 10 as a result of the ion-exchange process can lead to an increase in the maximum dimension d of particles 10, producing a more efficient embolization. In some embodiments, as a result of an ion-exchange process in coating 14, d can increase by 5% or more (e.g., 10% or more, 15% or more, 20% or more, 25% or more). In certain embodiments, d can increase by 50% or less (e.g., 45% or less, 40% or less, 35% or less, 30% or less).

Embolic particles 10 can be fabricated using various methods. For example, particles 10 can be fabricated using drop formation methods. A solution containing precursors of the material(s) of core 12 is delivered to a drop generator, which forms drops of the solution. The drops are transferred to a gelling vessel and contacted with a gelling agent, thereby stabilizing the drops. Subsequently, the drops are transferred to a reactor vessel, where they are hardened (e.g., by cross-linking). The gelling agent is removed, and the hardened particles are filtered. Drop formation methods are disclosed, for example, in U.S. patent application Ser. No. 10/651,475, now U.S. Publication No. US 2004/0101564, filed on Aug. 29, 2003 and entitled "Embolization", the entire contents of which are incorporated herein by reference.

Coating 14 can be applied to surfaces of embolic particle cores 12 (e.g., cores formed by the drop formation methods discussed above) by spraying or dipping the cores with/in a coating solution to form embolic particles 10. The coating solution can include one or more polymer materials or precursors of polymer materials, and one or more agents (e.g., therapeutic agents, reactive agents, imaging agents). Suitable polymer materials include any one or more of the materials used to form cores 12. Coating materials are generally disclosed, for example, in U.S. patent application Ser. No. 10/615,276, now U.S. Publication No. US 2004/0076582, filed on Jul. 8, 2003 and entitled "Agent Delivery Particle", the entire contents of which are hereby incorporated by reference.

Coating 54 can be formed of any of the materials suitable for forming coating 14. Coating 54 can be applied to surfaces of embolic coils by spraying or dipping to yield coated embolic coils.

Embolic particles and coils which bind to one another can be used to treat a variety of conditions. Particles and coils can be delivered to various sites in the body, including, for example, sites having cancerous lesions, such as the breast, prostate, lung, thyroid, or ovaries. The compositions can be used in, for example, neural, pulmonary, and/or AAA (abdominal aortic aneurysm) applications. The particles and coils can be used in the treatment of, for example, fibroids, tumors, internal bleeding, arteriovenous malformations (AVMs), and/or hypervascular tumors. The particles and coils can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted.

Figure 6A:
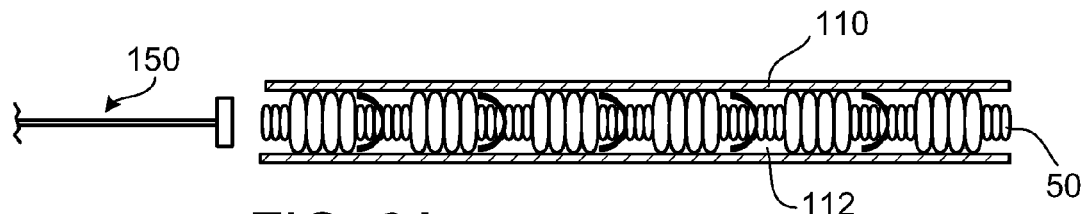
FIGS. 6A-6C are schematic diagrams that illustrate the delivery of an embodiment of an embolic coil into a vessel.
Figure 6B:
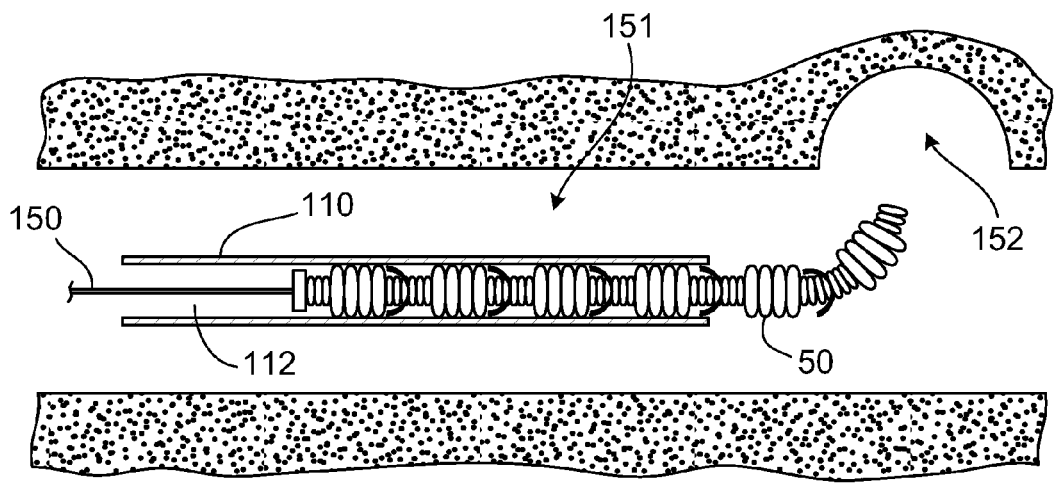
Figure 6C:
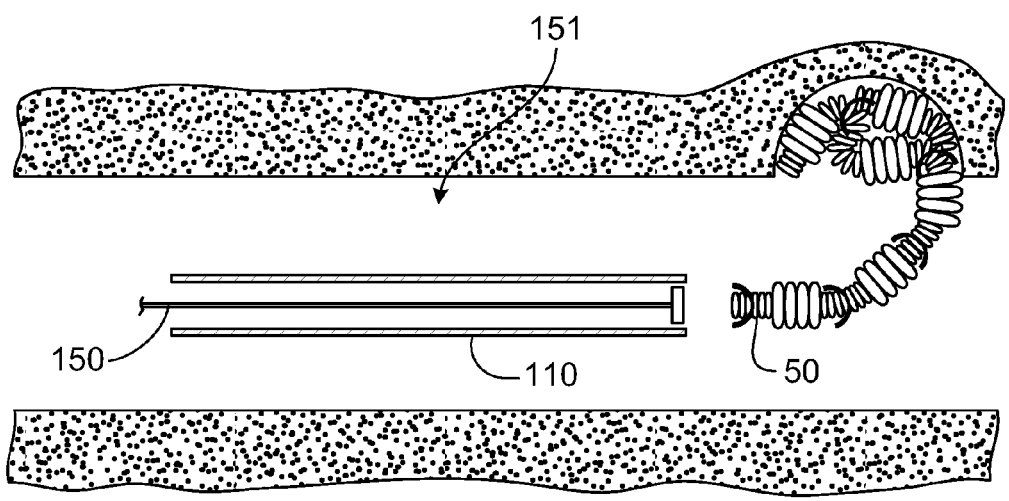

Typically, to initiate an embolization procedure at a body site, embolic coils are first delivered to the site. Embolic coils 50 can be delivered to a site as shown in FIGS. 6A-6C FIG. 6A shows embolic coil 50, loaded into lumen 112 of catheter 110, and a pusher wire 150 disposed outside of catheter 110. In some embodiments, embolic coil 50 can be disposed within a carrier fluid (e.g., a saline solution, a contrast agent, a heparin solution) while embolic coil 50 is within lumen 112 of catheter 110. In FIG. 6B, catheter 110 is delivered into a lumen 151 of a subject, and pusher wire 150 is inserted into lumen 112 of catheter 110, such that it contacts embolic coil 50. Pusher wire 150 is then used to push embolic coil 50 out of catheter 110 and into lumen 151. FIG. 6C shows embolic coil 50 filling a portion of lumen 151 (e.g., aneurismal sac 152) after embolic coil 50 has been pushed out of catheter 110 by pusher wire 150. By filling aneurysmal sac 152, embolic coil 50 helps to occlude aneurysmal sac 152.

The length embolic coil 50 when fully extended within lumen 112 of catheter 110 can generally be chosen as desired for particular embolization applications. For example, in some instances, using a single, relatively long coil rather than multiple shorter coils can reduce the time associated with an embolization procedure, and/or reduce the likelihood of complications associated with an embolization procedure. In some embodiments, the length of embolic coil 50 can be at least 0.5 cm (e.g., at least 2.5 cm, at least 5 cm, at least 10 cm, at least 15 cm, at least 20 cm), and/or at most 40 cm (e.g., at most 30 cm, at most 20 cm, at most 15 cm, at most 10 cm, at most 5 cm). In certain embodiments, the length of embolic coil 50 can be from 0.5 cm to 40 cm (e.g., from 2.5 cm to 30 cm, from 5 cm to 25 cm).

Embolic coils 50 are used, either alone or in combination with embolic particles 10, to embolize the body site. As discussed previously, when used together, embolic coils 50 and embolic particles 10 interact and bind with one another (e.g., by forming bonds such as ionic and/or covalent bonds), and particles 10 and coils 50 remain bound at the embolization site, increasing the efficiency of the embolization procedure.

Figure 7A:
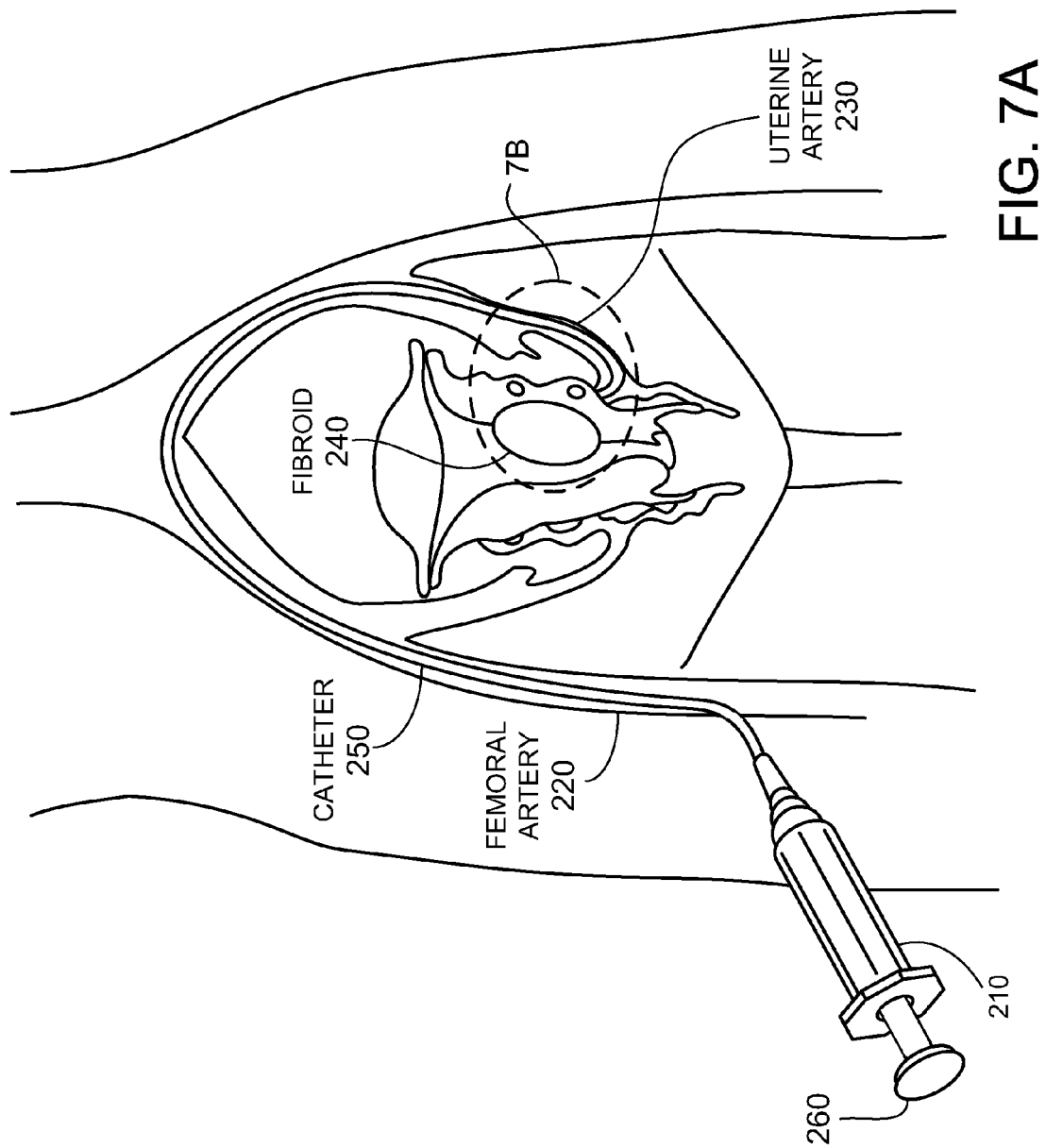
FIG. 7A is a schematic diagram illustrating an embodiment of a method of injecting a particle composition including embolic particles into a vessel.
Figure 7B:
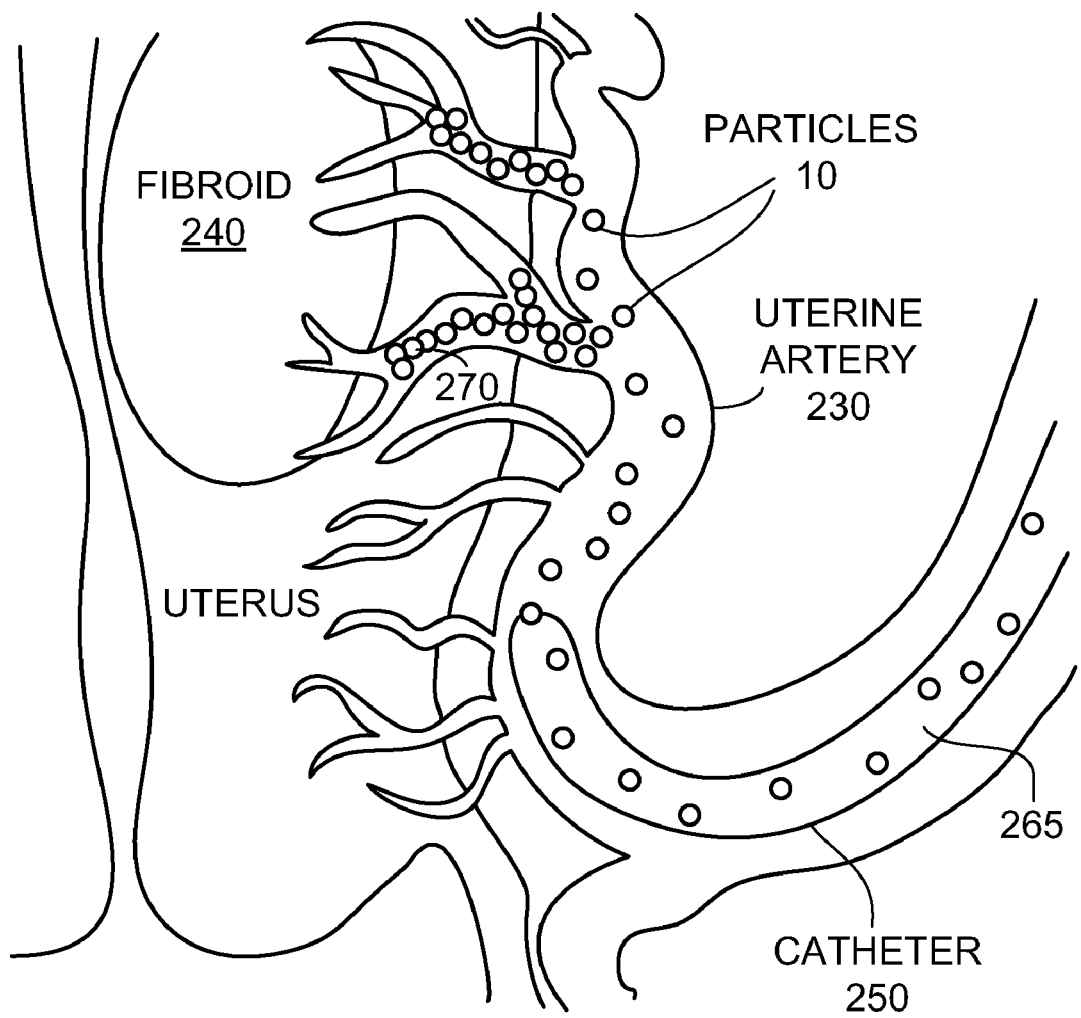
FIG. 7B is an enlarged view of region 7B in FIG. 7A.

To deliver embolic particles 10 to a body site following delivery of embolic coils 50, embolic particles 10 can be combined with a carrier fluid (e.g., a pharmaceutically acceptable carrier, such as a saline solution, a contrast agent, or both) to form a particle composition, which can then be delivered to the body site and used to assist in embolizing the site. FIGS. 7A and 7B illustrate the use of a particle composition to embolize a lumen of a subject. As shown, a particle composition including particles 10 and a carrier fluid is injected into a vessel through an instrument such as a catheter 250. Catheter 250 is connected to a syringe barrel 210 with a plunger 260. Catheter 250 is inserted, for example, into a femoral artery 220 of a subject. Catheter 250 delivers the composition to, for example, occlude a uterine artery 230 leading to a fibroid 240 located in the uterus of a female subject. The particle composition is initially loaded into syringe 210. Plunger 260 of syringe 210 is then compressed to deliver the particle composition through catheter 250 into a lumen 265 of uterine artery 230.

FIG. 7B, which is an enlarged view of section 7B of FIG. 7A, shows uterine artery 230, which is subdivided into smaller uterine vessels 270 (e.g., having a diameter of two millimeters or less) that feed fibroid 240. The particles 10 in the particle composition bind to coils 50, previously delivered to uterine artery 230, to partially or totally fill the lumen of uterine artery 230, either partially or completely occluding the lumen of the uterine artery 230 that feeds uterine fibroid 240.

Typically, although not necessarily, the embolic composition delivered to a body site includes both embolic particles 10 and embolic coils 50, and the magnitude of a dose of a composition that includes particles and/or coils can vary based on the nature, location and severity of the condition to be treated, as well as the route of administration. A physician treating the condition, disease or disorder can determine an effective amount of composition. An effective amount of embolic composition refers to the amount sufficient to result in amelioration of symptoms and/or a prolongation of survival of the subject, or the amount sufficient to prophylactically treat a subject. The compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

A composition can include a mixture of particles (e.g., particles formed of polymers including different weight percents of monomer units, particles having different types of coatings, particles including different types of therapeutic agents), and/or a mixture of coils (e.g., coils formed of different materials, coils having different types of coatings, coils that include different types of therapeutic agents). Alternatively, the particles and/or coils can all be of the same type. A physician can select a particular composition based on, for example, the type of procedure to be performed. In certain embodiments, a physician can use a composition with a relatively high concentration of particles during one part of an embolization procedure, and a composition with a relatively low concentration of particles during another part of the embolization procedure. Similarly, different concentrations of coils can be used during different parts of the embolization procedure.

Suspensions of embolic particles in saline solution can be prepared to remain stable (e.g., to remain suspended in solution and not settle and/or float) over a desired period of time. A suspension of particles can be stable, for example, for from one minute to 20 minutes (e.g. from one minute to 10 minutes, from two minutes to seven minutes, from three minutes to six minutes).

In some embodiments, embolic particles can be suspended in a physiological solution by matching the density of the solution to the density of the particles. In certain embodiments, the particles and/or the physiological solution can have a density of from one gram per cubic centimeter to 1.5 grams per cubic centimeter (e.g., from 1.2 grams per cubic centimeter to 1.4 grams per cubic centimeter, from 1.2 grams per cubic centimeter to 1.3 grams per cubic centimeter).

In certain embodiments, the carrier fluid for embolic particles and/or coils can include a surfactant. The surfactant can help the particles and/or coils to mix evenly in the carrier fluid and/or can decrease the likelihood of the occlusion of a delivery device (e.g., a catheter) by the particles and/or coils. In certain embodiments, the surfactant can enhance delivery of the particles and/or coils (e.g., by enhancing the wetting properties of the particles and/or coils and facilitating the passage of the particles and/or coils through a delivery device). In some embodiments, the surfactant can decrease the occurrence of air entrapment by the particles and/or coils (e.g., by porous particles and/or coils). Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, a particle composition can include from 0.05 percent by weight to one percent by weight (e.g., 0.1 percent by weight, 0.5 percent by weight) of a surfactant. A surfactant can be added to the carrier fluid prior to mixing with the embolic particles and/or coils, and/or can be added to the embolic particles and/or coils prior to mixing with the carrier fluid.

A number of embodiments have been disclosed above. In general, however, other embodiments are also possible. For example, in some embodiments, particle 10 may not have a coating 14, and may include only core 12. Core 12 can be formed from a material that causes particle 10 to bind to a surface of an embolic coil (e.g., embolic coil 50) in vivo. For example, core 12 can be formed from one or more of the materials disclosed above in connection with coating 14.

In certain embodiments, embolic coil 50 may not have a coating 54, and may include only core 52. Core 52 can be formed from a material that causes one or more particles 10 to bind to coil 50 (e.g., via one or more chemical reactions, electrostatic interactions, and/or magnetic interactions between the particles 10 and coil 50). Exemplary materials that can be used to form coil 52 include one or more of the materials disclosed above in connection with coating 54.

In some embodiments, embolic coil 60 can include fibers 62 that wrap around an outer surface of coil 60 to form a coating surrounding coil 60. Fibers 62 can be formed from a material (e.g., a polymer, or a non-polymer material) that causes one or more particles 10 to bind to coil 60. Typically, for example, fibers 62 can be formed from one or more of the materials disclosed in connection with coating 54. Embolic coils with fibers are disclosed, for example, in the following U.S. Patent Applications: Elliott et al., U.S. patent application Ser. No. 11/000,741, entitled "Embolic Coils", published on Jun. 1, 2006, as U.S. Publication No. US 2006/0116711; Buiser et al., U.S. patent application Ser. No. 11/311,617, entitled "Coils", filed on Dec. 19, 2005; Buiser et al., U.S. patent application Ser. No. 11/458,156, entitled "Embolic Coils", filed on Jul. 18, 2006; Buiser et al., U.S. patent application Ser. No. 11/430,602, entitled "Embolic Coils", filed on May 9, 2006; Buiser et al., U.S. patent application Ser. No. 11/248,033, entitled "Coil Assemblies, Components and Methods", published on Apr. 12, 2007, as U.S. Publication No. US 2007/0083226; and Buiser et al., U.S. patent application Ser. No. 11/248,493, entitled "Embolic Coil Introducer Sheath Locking Mechanisms", published on Apr. 12, 2007, as U.S. Publication No. US 2007/0083219. The entire contents of each of the foregoing applications are incorporated herein by reference.

Other embodiments are in the claims.

What is claimed is:

1. An article, comprising:
   a particle including a coating; and
   an embolic coil including a coating,
   wherein the particle has a maximum dimension of at most 5,000 microns, and the coating of the particle is bound to the coating of the embolic coil, and
   wherein the coating of the particle comprises a first material, the coating of the embolic coil comprises a second material, and the first and second materials are capable of undergoing an acid-base reaction, the first and second materials are capable of undergoing a Michael addition, the first and second materials are capable of undergoing an isocyanate-alcohol reaction, or the first and second materials are capable of undergoing an azide-alkyne reaction.

2. The article of claim 1, wherein the particle has a maximum dimension of at least 100 microns.

3. The article of claim 1, wherein the coating of the particle is ionic.

4. The article of claim 3, wherein the coating of the embolic coil is ionic.

5. The article of claim 4, wherein the coating of the particle has a charge that is opposite to a charge of the coating of the embolic coil.

6. The article of claim 1, wherein the coating of the particle is ionically bound to the coating of the embolic coil.

7. The article of claim 1, wherein the coating of the particle is covalently bound to the coating of the embolic coil.

8. The article of claim 1, wherein the embolic coil includes fibers.

9. An article, comprising:
   a particle including a ligand; and
   an embolic coil including a ligand,
   wherein the particle has a maximum dimension of at most 5,000 microns, and the ligand of the particle is bound to the ligand of the embolic coil.

10. The article of claim 9, wherein the ligand of the embolic coil and the ligand of the particle are ionically bound.

11. The article of claim 9, wherein the ligand of the embolic coil and the ligand of the particle are covalently bound.

12. The article of claim 9, wherein the ligand of the particle comprises a first material, the ligand of the embolic coil comprises a second material, and the first and second materials are bound via a reaction product of: a) an acid-base reaction, a Michael addition, an isocyanate-alcohol reaction, an azide-alkyne reaction, or a biotin-avidin complex.

13. The article of claim 10, wherein the embolic coil includes fibers.

* * * * *

UNITED STATES PATENT AND TRADEMARK OFFICE
CERTIFICATE OF CORRECTION

PATENT NO. : 7,901,704 B2
APPLICATION NO. : 12/193462
DATED : March 8, 2011
INVENTOR(S) : Robert E. Richard Page 1 of 1

It is certified that error appears in the above-identified patent and that said Letters Patent is hereby corrected as shown below:

On the title page under item (56), Column 2, Other Publications, line 4: delete "druck" and insert --drug--.

On the title page under item (56), Column 2, Other Publications, line 17: delete "Copper(I)-Catalzed" and insert --Copper(I)-Catalyzed--.

Signed and Sealed this
Tenth Day of May, 2011

David J. Kappos
*Director of the United States Patent and Trademark Office*